United States Patent [19]

Takata et al.

[11] Patent Number: 4,609,461
[45] Date of Patent: Sep. 2, 1986

[54] APPARATUS FOR PURIFYING BLOOD

[75] Inventors: Satoshi Takata, Kobe; Nobutaka Tani, Minoo, both of Japan

[73] Assignee: Kanegafuchi Kagaku Kogyo Kabushiki Kaisha, Osaka, Japan

[21] Appl. No.: 638,084

[22] Filed: Aug. 6, 1984

[30] Foreign Application Priority Data

Aug. 8, 1983 [JP] Japan .................. 58-145590

[51] Int. Cl.4 ............................................ B01D 13/00
[52] U.S. Cl. .................. 210/195.2; 210/259; 210/434
[58] Field of Search .............. 210/648, 434, 433.2, 210/321.1, 321.2, 195.2, 259

[56] References Cited

U.S. PATENT DOCUMENTS 3,228,877  1/1966  MahUn ................................ 210/22
3,669,878  6/1972  Marantz et al. ................... 210/648 X
4,243,532  1/1981  Tsuda et al. ...................... 210/434 X Primary Examiner—Frank Spear
Attorney, Agent, or Firm—Armstrong, Nikaido, Marmelstein & Kubovcik

[57] ABSTRACT

An apparatus for purifying blood which is able to separate blood into plasma and blood rich in blood cells, to purify the separated plasma and to mix the purified plasma into the blood stream simultaneously by itself.

The apparatus has two parts, i.e. a blood flowing system in which the blood is separated by means of porous hollow fibers provided in a container and the purified plasma is mixed into the blood stream through the hollow fibers, and a plasma flowing path in which the separated plasma is circulated and purified at a plasma purifying device provided on the way of the path.

The apparatus has a simple structure and can be operated without any specific cares and difficulty. The apparatus is free from any problems, for instance, hemolysis, fiber blockage, mixing of the purifier particles into blood, and the like.

2 Claims, 6 Drawing Figures

APPARATUS FOR PURIFYING BLOOD

BACKGROUND OF THE INVENTION

The present invention relates to an apparatus for purifying blood, which is useful for eliminating unnecessary or impure substances from the blood of a patient and purifying the blood.

In recent years, as a method for purifying the blood, a method has been broadly used, in which plasma is separated from blood, unnecessary substances are eliminated from the plasma to purify it, and then, the purified plasma is returned into a patient body.

The above method has advantages that there is no possibility of infection in comparison with a plasma-exchange treatment and that a loss and a damage of blood cells are less in comparison with a direct hemoperfusion treatment, in which blood is directly contacted with a purifier or the like to eliminate the unnecessary substances.

The method consists of three processes, i.e. a process for separating blood into plasma and blood rich in blood cells (a plasma-separating process), a process for purifying the plasma by passing through a purifying device to eliminate the unnecessary substances (a purifying process) and a process for mixing the purified plasma with the blood rich in blood cells (a mixing process).

A continuous centrifugation or a porous membrane can be used in the plasma-separating process to separate the blood, and recently, a plasma-separator employing a porous hollow fiber which is relatively easy to handle has been broadly used. However, even in those cases, scrupulous attention must be paid at the beginning of a blood circulation outside the body (a priming period), and an operation is necessary, that a plasma filtration rate is gradually increased to a steady state with controlling a balance between the plasma filtration rate and the blood flow rate. If such an operation is faultily handled, various problems such as hemolysis and blocking of the membrane will be caused. Such problems will eventually cause the decrease of plasma filtration rate. Further, it is necessary to maintain a trans membrane pressure within a definite range, and when it is neglected, the same problems as described above will also occur. As mentioned hereinbefore, a conventional plasma-separating process has a drawback that its operation is complicated and skilled technics are required for the operation.

In the purifying process, a removing device is used to eliminate the unnecessary substances which consists of a container charged with a purifying agent such as an ion exchange resin or an immunological adsorbent or an adsorbent prepared by fixing a material having an affinity for the unnecessary substances to a water-insoluble carrier. However, a conventional apparatus for purification of blood such as the apparatus disclosed in Japanese Examined Patent Publication (Tokkyo Kokoku) No. 22107/1980 has several problems. Hereinafter, the problems are explained with reference to FIG. 1.

FIG. 1 is a block diagram showing a conventional apparatus for a purification of blood, wherein a blood-circulating pump 1, a plasma separator 2, a plasma pump 3, a plasma purifying device 4 and a mixing vessel 5 are connected so that the blood flows into the separator 2 like an arrow A and flows out from the vessel 5 like an arrow B.

Plasma separated at the separator 2 is transferred to the purifying device 4 by means of the pump 3, whereby the plasma has only one chance to contact with a plasma purifier in the device 4 after separated from the blood. It is not until the time when the plasma is mixed with blood rich in blood cells at the mixing vessel 5, and the blood is once returned into a body, taken out from the body again and subjected to a separation at the separator 2, and then, the separated plasma is transferred to the device 4 again, that the plasma which is not sufficiently purified can come in the next contact with the purifier.

Consequently, as long as employing the circulating path as shown in FIG. 1, for the purpose of improving the purification efficiency, there is no other way except that a purifier having an extremely good purification ability is used, that a large amount of a purifier is charged in the device or that a contact time is increased by lowering the taking speed of plasma. However, when a purifier is charged in the device in a large amount, an amount of blood and plasma outside the body is increased during the circulation, and a patient is exposed to a dangerous condition. When the plasma flow rate is lowered, a treating time becomes longer and it is disadvantageous. Therefore, a purifier usable in the purifying apparatus described above is limited to a purifier which has a high purification rate.

Moreover, the purifying apparatus shown in Fig. 1 has a serious problem that there is a danger that the purifier flows into the blood stream. As the purifier, a purifier in the form of particle is generally used, and there is a possibility that purifier particles or the broken pieces thereof leak from the purifying device 4 by the plasma current and flow into the blood on the plasma current. For the purpose of avoiding such a danger, it is required to provide a filter at an inlet and an outlet of the purifying device.

SUMMARY OF THE INVENTION

For the purpose of solving many problems as described above, the present inventors have studied earnestly and have found a surprising fact. Hereinafter, a principle of the present invention is explained referring to FIG. 2.

FIG. 2 is a schematic diagram to explain the principle. A plasma separator was made using a porous hollow fiber. A blood flowed into the separator in the direction of an arrow C and flowed out from the separator in the direction of an arrow D. The separated plasma was taken out from a plasma reservoir via an outlet 6, and via an inlet 10, was introduced isotonic sodium chloride solution 9 into the plasma reservoir. A taking pump 7 and an injecting pump 8 were provided on the way of the taking path and injecting path, respectively. The pumps 7 and 8 were running at the same speed to obtain a taking amount of plasma equal to that in case of an actual treatment. At 1 hr after an experiment started, there was found little sign that the isotonic sodium chloride solution introduced via the inlet 10 was mixed in the plasma flowing out from the plasma reservoir via the outlet 6. The plasma taken out via the outlet 6 had almost the same components as that of the plasma in an original blood, i.e. at least 70 to 80% of the total proteins flowed out via the outlet 6. That is, the present inventors have found a fact that almost all the isotonic sodium chloride solution introduced via the inlet 10 flowed into the blood stream via the pores of the hollow fibers.

The present invention makes use of such a fact, i.e. a plasma purifying device is provided between the pumps 7 and 8, whereby the purified plasma does not flow into a direction toward the outlet 6 but flows into the blood stream, via the porous hollow fibers so that a purified blood flowing out from the separator via an outlet in the direction of an arrow D is obtained.

In accordance with the present invention, there is provided an apparatus for purification of blood comprising (A) a blood flowing system including a plasma separating device having a blood inlet, a blood outlet from which purified blood flows out, at least one plasma reservoir between said inlet and outlet which has at least one plasma outlet and inlet locating close to said blood inlet and outlet, respectively, and (B) a plasma flowing path including at least one plasma purifying device, which allows plasma to flow from said plasma outlet of said plasma separating device to said plasma inlet via said plasma purifying device; said plasma separating device is made up of said blood inlet, said blood outlet from which purified blood flows out and said plasma reservoir surrounded by a container, an impure blood room and a purified blood room; in said plasma reservoir are enclosed porous hollow fibers; and said blood inlet and said blood outlet are connected by said porous hollow fibers;

so that the blood flowing into said plasma separating device via said blood inlet is separated into the plasma, the plasma is taken out through said plasma outlet to said plasma purifying device and purified at said plasma purifying device, the purified plasma is returned to said plasma reservoir through said plasma inlet and passes through said porous hollow fibers to mix with blood.

DETAILED DESCRIPTION

Hereinafter, an apparatus for purifying blood of the present invention is explained referring to the attached drawings showing an embodiment, respectively.

Figure 1:
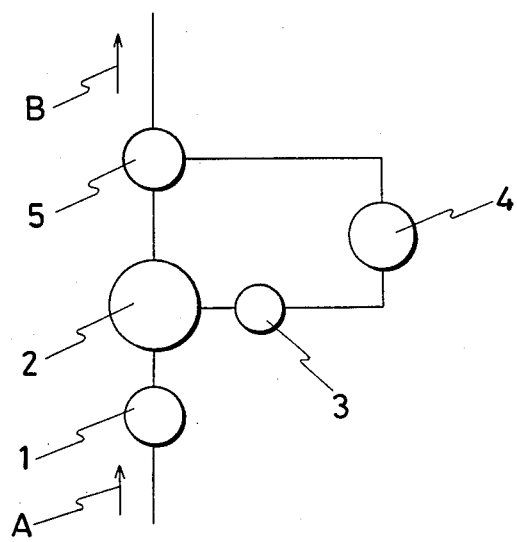
FIG. 1 is a block diagram of a conventional apparatus for a purification of blood.
Figure 2:
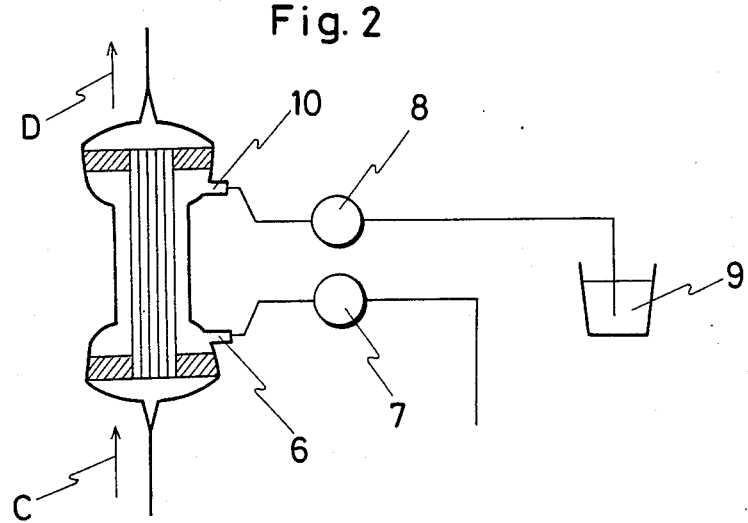
FIG. 2 is a schematic diagram to explain the principle of the invention.
Figure 3:
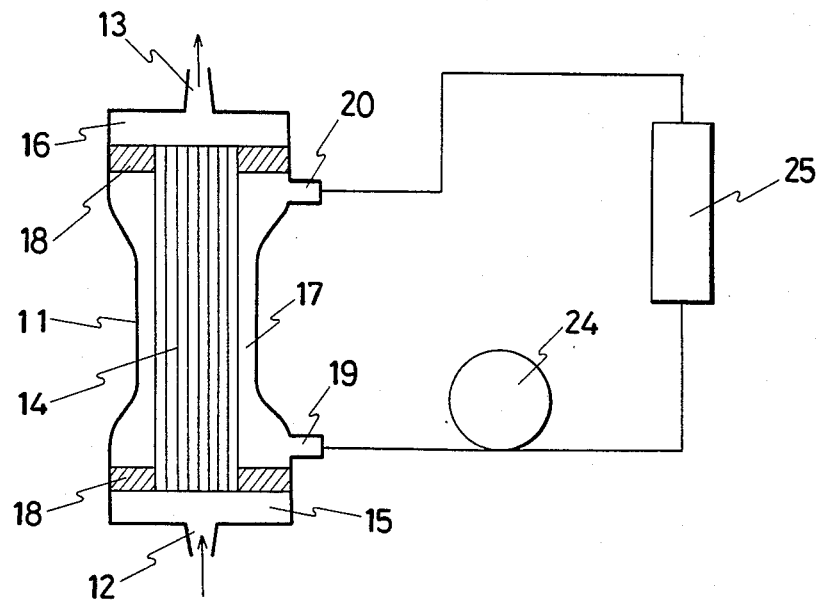
FIG. 3 is a flow chart of an embodiment of the invention.

FIG. 3 shows a flow chart of an embodiment of an apparatus for purifying blood in accordance with the invention. A plasma separator is shown in the longitudinal section. Arrow heads in the chart show a flow of blood. In FIG. 3, the numbers 11, 18 and 19 represent a container, a sealant and a plasma flow outlet, respectively, and other numbers will be explained hereinafter.

Blood is introduced via blood flow inlet 12 into an impure blood room 15 by means of an external blood circulation pump (not shown) and is separated into blood having a high concentration of blood cells and plasma during passing through a bunch of hollow fibers 14 due to a flow inlet pressure.

At that time, a pressure difference corresponding to a pressure drop caused by the bunch of hollow fibers arises between the impure blood room 15 and a purified blood room 16 and also the blood pressure in the bunch of hollow fibers changes by a gradation that the blood pressure of a nearer point to the inlet 12 is higher.

When a plasma circulation pump 24 is not operated, at the side of the inlet 12 of the bunch of hollow fibers 14, a filtration proceeds because of the higher blood pressure in the hollow fibers and at the side of a blood flow outlet 13, near a plasma flow inlet 20, plasma flows back into the hollow fibers because of the lower pressure in the hollow fibers than that in a plasma reservoir 17. In a conventional system, the pressure in the plasma reservoir was kept lower than that in the hollow fibers, because plasma was extracted and fed via purifying device into a mixing device.

In the apparatus of the present invention, since the extracted plasma is fed via plasma purifying device 25 into the plasma reservoir 17 of the plasma separator, the pressure in the plasma reservoir 17 is almost kept to the middle between the pressure near the inlet 12 of the bunch of hollow fibers 14 and the pressure near the outlet 13 of the bunch of the hollow fibers 14.

Therefore, according to the invention, the purified plasma flows back into the hollow fibers and is mixed with blood by passing through the pores of the hollow fibers, and the purified plasma flows out as purified blood through the outlet 13.

In the present invention, a pressure gradient in the hollow fibers arising at the time when blood flows in the hollow fibers is utilized as a driving force for the separation and recombination of blood and plasma. Therefore, as long as the blood circulation pump is appropriately operated, any troubles including hemolysis and fiber blockage resulted from a too much difference between the pressures of an inside and an outside of a membrane of the fiber are scarcely occurred even if the plasma circulation pump 24 is operatied in any ways. Further, since plasma which passed through the purifying device 25 and blood are divided by a wall of the porous membrane of the hollow fibers, broken pieces or fine particles of the plasma purifiers in the purifying device 25 are prevented from flowing into and mixing with blood. Even if a great deal of such a piece or particle should leak out from the device 25, treatment could be continued free from the fiber blockage because of a large outside surface area of the hollow fibers.

Plasma purifiers usable in the present invention are not fundamentally limited in a charging density or a kind. Even a plasma purifier, which is not able to be applied because of its low purifying rate, can be applicable when the plasma circulation pump 24 is operated at a high speed, to circulate plasma rapidly between the plasma reservoir 17 and the plasma purifying device 25 substantially many times, and to increase contact chances of plasma with the purifiers. Conventional known purifiers, for example, activated carbon, alumina, ion exchange resin, adsorbent made of a water-insoluble carrier holding materials having affinity for the objects to be removed are, of course, applicable. Moreover, a purifier containing immobilized enzymes is also applicable which eliminates the objects to be removed by a chemical reaction, regardless of its reaction rate.

As the objects to be removed, there can be exemplified, for example, waste products, LDL cholesterol, protein bound toxin, various causal objects of diseases related to immunity including an immune complex of an autoantibody, and the like.

A porous hollow fiber usable in the present invention is a porous hollow fiber having a high plasma permeation rate and inhibiting a pass of blood cells, and in case of using such a fiber, a satisfactory purification of blood can be achieved. A porous hollow fiber having a diameter of pores at the inside surface of 0.01 to 10 μm, preferably 0.1 to 2 μm and a permeation rate for pure water not less than 2 ml/m$^2$.min.mmHg, preferably of 50 ml/m$^2$.min.mmHg is advantageously used. When the diameter of pores is not more than 0.01 μm, a permeation rate of the objects to be removed is small and a purification efficiency is remarkably lowered. On the contrary, when the diameter of pores is not less than 10 μm, a blood cell passes through the hollow fiber or blocks the pores of the hollow fiber. When the permeation rate for pure water is not more than 2 ml/m$^2$.min.mmHg, too many hollow fibers are necessary in order to effectively purify blood, and as the result, the amount of blood and plasma outside a body is increased during the extracorporeal circulation.

According to the present invention, an inner diameter of the hollow fiber is suitably 250 to 500 μm and about 2,000 to 4,000 hollow fibers having such an inner diameter are preferably used in the form of a bunch.

The material for the hollow fiber is not limited to any specific materials, as long as it meets the above-mentioned requirements. Typical examples of such a material are, for instance, cellulose acetate, polypropyrene, polysulfone, polycarbonate, polyethylene, polyvinylalcohol, ethylene-vinylalcohol copolymer, polyacrylonitrile, polyamide, and the like.

Figure 4:
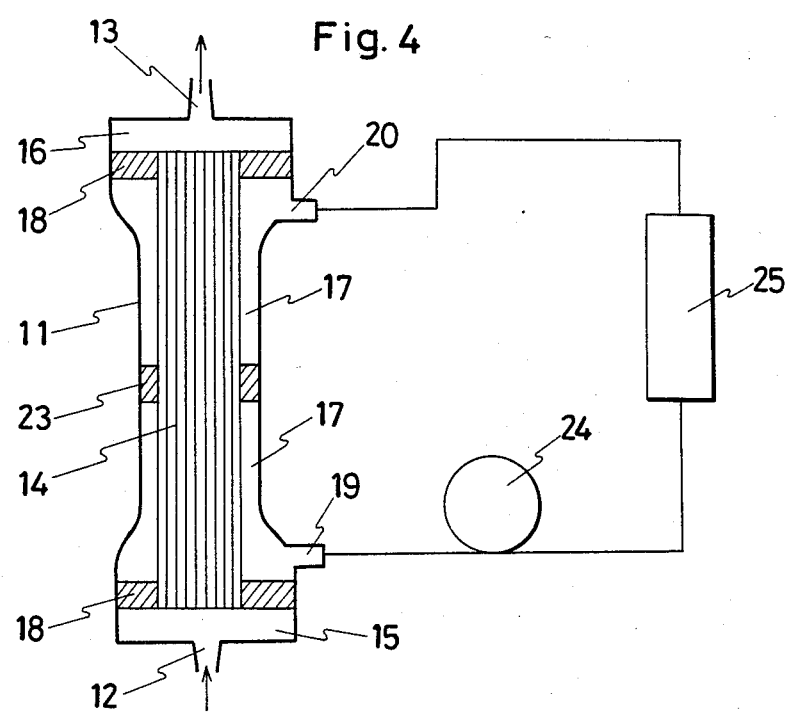
FIG. 4 and FIG. 5 are another embodiments of the invention, respectively.

FIG. 4 shows another enbodiment of the present invention, wherein the same number as in FIG. 3 represents the same member. An apparatus of FIG. 4 is the same as that of FIG. 3 except that the plasma reservoir 17 is divided by a partition plate 23 between the plasma flow outlet 19 and the plasma flow inlet 20. The apparatus shown in FIG. 4 is particularly suitable in case that the plasma purifier has an excellent purification efficiency. The plasma circulating pump 24 can be operated at the necessary lowest speed because the purified plasma is scarcely mixed with the impure plasma in the plasma reservoir 17. Moreover, even when the plasma circulating pump 24 is operated at an excess high speed, a trouble such as hemolysis or fiber blockage can be prevented since the purified plasma flows through the hollow fibers into the other reservoir part near the plasma flow outlet 19. Needless to say, the broken pieces and the particles of the purifiers can be prevented from mixing into the blood stream.

Figure 5:
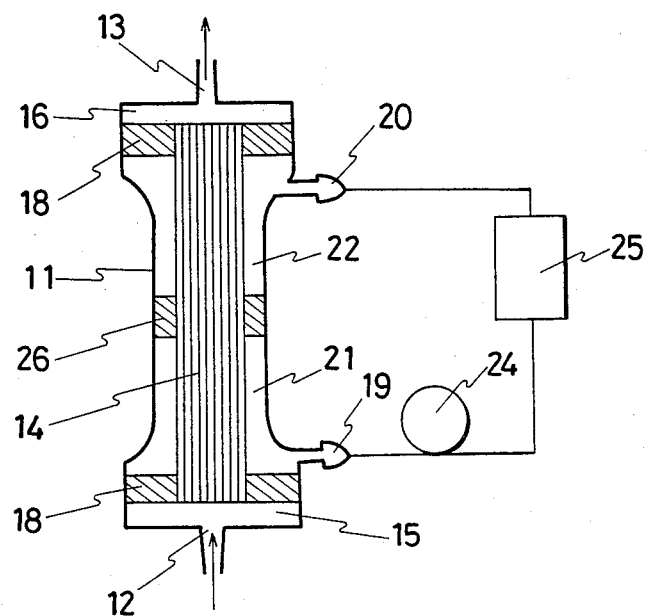

FIG. 5 shows further another embodiment of the apparatus of the invention, wherein the same number as in FIG. 3 and FIG. 4 represents the same member. The apparatus shown in FIG. 5 is suitable in case that the plasma circulating pump 24 is operated with a sufficient care. Referring to FIG. 5, the plasma reservoir is completely divided into a purified plasma reservoir 22 and an impure plasma reservoir 21 by charging a sealant 26 at the middle part of the bunch of hollow fibers 14, and the blood stream can pass through the hollow fibers. In that case, one of the important features of the present invention that the broken pieces and the particles of the purifiers is prevented from mixing into the blood stream can also be exhibited.

Further, when two porous partition plates are provided at the middle part of the bunch of hollow fibers 14 leaving a certain space between them in the container 11 and the plasma purifiers are charged in the space, the contact chance between the plasma and the purifiers can be further increased.

As explained hereinbefore, the apparatus for purifying blood of the present invention is able to achieve the following three epochal effects simultaneously.

(1) With respect to the circulating pump, only one pump should be carefully controlled while conventionally two pumps should be carefully controlled.

(2) The danger that the broken pieces and the particles of the purifiers are mixed into the blood can be avoided.

(3) The purifier having an inferior purifying efficiency can also be applicable.

The present invention is more specifically described and explained by means of the following Examples. It is to be understood that the present invention is not limited to the Examples, and various changes and modifications may be made in the invention without departing from the spirit and scope thereof.

EXAMPLE 1

Using the apparatus as shown in FIG. 3, the waste products were removed from fresh cow blood.

In a container having a length of 23 cm and an outer diameter of 25 mm, was provided a bunch of hollow fibers consisting of 2,700 porous hollow fibers of polysulfone having an outer diameter of 400 μm, an inner diameter of 300 μm, a diameter of pores at the inside surface of 0.2 μm, a diameter of pores at the outside surface of 0.8 μm and a permeation rate for pure water of 500 ml/m$^2$.min.mmHg, and the both ends of the bunch were fixed to the container with sealants of polyurethane, respectively. A plasma flow outlet and a plasma flow inlet were provided in the container, and they were connected to a plasma circulating system as shown in FIG. 3, respectively. 200 g of activated carbon of 25 to 40 mesh was used as the purifier.

Using the thus constructed apparatus, 4 l of fresh cow blood was circulated at a flowing rate of 100 ml/min by means of a blood circulating pump and a plasma circulating pump was operated to give a flowing rate of plasma of 25 ml/min. The blood which was obtained at the blood flow outlet had concentrations of uric acid and creatinine decreased by 68% and 70% in comparison with those in the blood at the blood flow inlet, respectively.

EXAMPLE 2

Using the apparatus as shown in FIG. 3, cholesterol was removed from blood of a rabbit of hyperlipemia.

In a container of polycarbonate having a length of 16 cm, an outer diameter of 13 mm and an inner diameter of 9 mm, was provided a bunch of hollow fibers consisting of 240 porous hollow fibers of polysulfone having an outer diameter of 400 μm, an inner diameter of 300 μm, a diameter of pores at the inside surface of 0.2 μm a diameter of pores at the outside surface of 0.8 μm and a permeation rate for pure water of 500 ml/m$^2$.min.mmHg, and the both ends of the bunch were fixed to the container with sealants of polyurethane, respectively. A plasma flow outlet and a plasma flow inlet were provided in the container adjacent to the sealants, respectively.

Dextran sodium sulfate was fixed to porous cellulose gel commercially available from CHISSO CORPORATION under the commercial name of CSK A-3 (removable maximum molecular weight: 50,000,000, particle size: 45 to 105 μm) by the method described in Japanese Patent Application No. 70267/1983. The fixed amount of dextran sodium sulfate was 3 mg per 1 ml of the gel.

The obtained gel was charged in a column having an inner diameter of 22 mm and a length of 66 mm (volume: 25 ml) provided with meshes at both ends thereof to give a plasma purifying device capable for removing a low-density lipoprotein.

Figure 6:
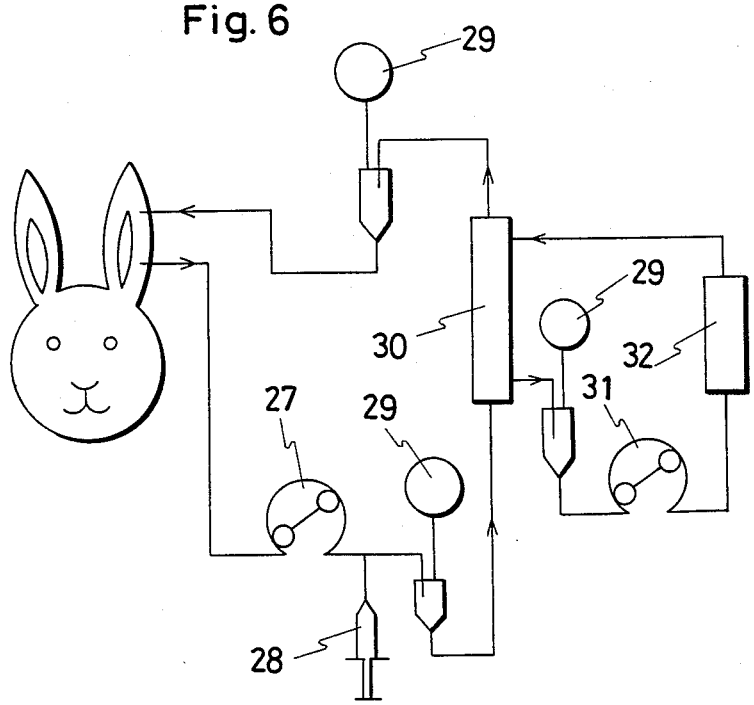
FIG. 6 is a block diagram showing the experiment using the apparatus of the invention.

Using a WHHL rabbit of hyperlipemia, a blood circulating path outside the body was formed as shown in FIG. 6. A blood circulating pump 27, Hepason's injector 28, pressure gages 29, a plasma separator 30, a plasma circulating pump 31 and a plasma purifying device 32 were connected as shown in FIG. 6. The blood was circulated outside the body at a flowing rate of blood of 6 ml/min and at a flowing rate of plasma of 2 ml/min for 2 hrs. As the result, a total cholesterol in the blood was decreased from 500 mg/dl to 190 mg/dl.

What we claim is:

1. An apparatus for the purification of whole blood comprising:

(a) a chamber having an inlet at one end therof, an impure blood room formed in said chamber adjacent to said inlet and being separated from the remainder of said chamber by a first separation means, an outlet at the end of said chamber opposite from said inlet, a purified blood room formed in said chamber adjacent to said outlet and separated from the remainder of the chamber by a second separating means, a plurality of semi-permeable hollow fibers provided in said chamber and attached at their respective ends to the first separating means and the second separating means, a central reservoir formed in said chamber between said first and second separating means and around said hollow fiber membranes, said reservoir having a inlet adjacent to said purified blood room and an outlet adjacent to said impure blood room and allowing plasma to flow therein; and (b) a plasma treatment path consisting of a pump connected to said outlet of said plasma reservoir, a plasma purifying means connected to the outlet of said pump and means for connecting the output of said purifying means to the inlet of said plasma reservoir; and wherein said hollow fibers are capable of separating plasma from whole blood and having pores at the inside surface thereof of 0.01 to 10 $\mu$m in diameter and a permeation rate for pure water of not less than 2 ml/m$^2$.min.mmHg.

2. The apparatus of claim 1, wherein when impure blood is introduced to the inlet of the chamber, the pressure difference between the inside of the hollow fibers and the central reservoir at an end adjacent to the impure blood room is larger than the pressure at which filtration occurs, and the pressure difference between the central reservoir and the inside of the hollow fibers at an end adjacent to the purified blood room is larger than the pressure at which the purified plasma flows back into the hollow fibers.

* * * * *